United States Patent
Middleton

[11] Patent Number: 5,899,901
[45] Date of Patent: May 4, 1999

[54] SPINAL FIXATION SYSTEM

[76] Inventor: Jeffrey Keith Middleton, 132 Gathurst Lane, Shevington, Nr. Wigan, Lancashire WN6 8HS, United Kingdom

[21] Appl. No.: 08/551,367

[22] Filed: Nov. 1, 1995

Related U.S. Application Data

[63] Continuation of application No. 08/150,094, filed as application No. PCT/GB92/00898, May 18, 1992, abandoned.

[30] Foreign Application Priority Data

May 18, 1991 [GB] United Kingdom .................... 9110778

[51] Int. Cl.$^6$ .................................................. A61B 17/56
[52] U.S. Cl. ............................. 606/61; 606/73; 606/105; 606/102
[58] Field of Search .................. 606/60, 61, 72, 606/73, 80, 86, 90, 102, 104, 105; 81/436, 448, 449; 600/57, 54

[56] References Cited

U.S. PATENT DOCUMENTS

| | | | |
|---|---|---|---|
| 2,002,021 | 5/1935 | Rouse | 606/105 |
| 3,286,749 | 11/1966 | Learned | 81/448 |
| 4,763,644 | 8/1988 | Weldo | 606/61 |
| 4,945,914 | 8/1990 | Allen | 606/54 |
| 4,955,885 | 9/1990 | Meyers | 606/61 |
| 5,059,194 | 10/1991 | Michelson | 606/57 |
| 5,152,790 | 10/1992 | Rosenberg et al. | 606/73 |
| 5,176,680 | 1/1993 | Vignaud et al. | 606/61 |
| 5,242,448 | 9/1993 | Pettine et al. | 606/102 |
| 5,353,667 | 10/1994 | Wilner | 81/436 |

FOREIGN PATENT DOCUMENTS

| | | | |
|---|---|---|---|
| 0528706 | 7/1992 | European Pat. Off. | 606/61 |
| 9414384 | 7/1994 | WIPO | 606/61 |

*Primary Examiner*—Michael Buiz
*Assistant Examiner*—Mark S. Leonardo
*Attorney, Agent, or Firm*—Richard E. Jenkins; Jeffrey L. Wilson; Jennifer L. Skord

[57] ABSTRACT

This invention relates to apparatus for use in surgery. More specifically, it relates to a spinal fixation device which is adapted to engage a spinal body (e.g. vertebra, or sacrum) and to grip an elongate part, which may be a rod, bar, wire or the like. for convenience. Two or more such devices may engage respective vertebrae and grip a common rod, which may act to improve a spinal defect, such as ankylosing spondylitis, lumbar scoliosis or spondylolisthesis. The invention also relates to surgical instrumentation for use with such a spinal fixation device.

32 Claims, 6 Drawing Sheets

SPINAL FIXATION SYSTEM

This is a continuation of application Ser. No. 08/150,094 filed on Apr. 5, 1994 now abandoned, which is a 371 of PCT/GB92/00898 filed May 18, 1991.

This invention relates to apparatus for use in surgery. More specifically, it relates to a spinal fixation device which is adapted to engage a spinal body (e.g. vertebra, or sacrum) and to grip an elongate part, which may be a rod, bar, wire or the like. For any such elongate part, the term "rod" will hereinafter be used, for convenience. Two or more such devices may engage respective vertebrae and grip a common rod, which may act to improve a spinal defect, such as ankylosing spondylitis, lumbar scoliosis or spondylolisthesis. The invention also relates to surgical instrumentation for use with such a spinal fixation device.

A spinal fixation device which has already been proposed comprises:

1. A spinal body engagement part (hereinafter called a "screw") comprising a threaded shank to engage with a vertebra, and a head to project from the spinal body, in use, the head being formed with a passage, conveniently a slot open to the top of the head and extending across the width of the head, into which a rod which extends transversely of the screw may be moved.
2. A rod-clamping element (hereinafter called a "pad") which can be introduced into the head. When the passage is a slot as described above, the movement is longitudinally of the screw to overlie the rod, the pad being unable to leave the slot other than by reverse longitudinal movement. To this end, the head has a central bore, formed longitudinally of the screw. In plan view the pad is circular and it may be slid down the bore but is of too large a diameter to pass transversely out of the slot. When the head has a slot the bore is suitably coincident therewith.
3. An externally threaded securement member (hereinafter called a "plug") which can be screwed into the bore to cause the rod to be firmly gripped between the bottom of the passage and the pad.

Because the rod to be clamped is preferably cylindrical, the bottom of the passage and the bottom face of the pad are preferably both curved, to match the curvature of the rod.

In accordance with a first aspect of the prevent invention, there is provided a spinal fixation system incorporating a prior device as described above, and a pad handling tool, wherein the pad has means for engagement with the pad handling tool. Such means for engagement are suitably for mechanical engagement and may comprise an externally threaded projection from its upper face or an internally threaded bore open to its upper face. By means of such a projection or bore a pad handling tool with a complementary threaded end may be employed, to assist the location of the pad in the bore of the head of the screw, and to assist the removal of a pad therefrom should that be required.

It will be appreciated that by such means, the handling of such pads is made much easier, compared with the handling of the earlier pads. The pads are very small, and difficult to handle manually or with forceps, even under non-operation conditions. The earlier pads are extremely difficult to handle, and engage correctly within the bores of the screws, during an operation. Moreover, removal of the earlier pads, should that be required, is also very difficult. By means of the first aspect of the present invention, such problems are virtually eliminated. A pad, carried on the end of a pad handling tool, may simply be pushed down into the bore of a screw. The tool may then be unscrewed from the pad; the pad will not turn because of the location of its curved bottom face around the rod. For removal, the tool may be screwed onto the pad, and the pad then withdrawn from the bore.

Whilst a pad with an externally threaded projection could be designed, or other means for engagement, e.g. a bayonet fitting, a pad with an internally threaded bore is preferred. Most conveniently, this is a through bore, extending to the bottom, curved, face.

Preferably, the aforementioned plug has two ends of identical form, both adapted to receive within them an engagement portion of a plug insertion tool. For example, both ends may be of square-socket or, preferably, of hexagonal-socket form. Suitably, this may be achieved by means of a square-section or hexagonal-section throughbore through the plug. In the prior devices one end of the plug was slotted, for receipt of a screwdriver head, or formed with flats, for engagement with a spanner, at one end only. It will be appreciated that a screwdriver drive is not particularly positive, and that slippage of the screwdriver is potentially disastrous, whilst there are space limitations during an operation which make use of a spanner difficult. In the novel plug the drive is non-slip and apace-efficient, whilst the provision for drive at either end of the plug is advantageous because the surgeon does not have to check how the plug should be inserted; either way will do.

For use with a plug of the spinal fixation system, there may be provided two plug insertion tools: a plug introducer tool for introducing a plug into the bore of a screw; and a plug securement tool for moving a plug introduced into the bore, to its location where it bears against the pad such that the rod is firmly gripped between the pad and the bottom of the passage. A plug introducer tool has a head adapted to be received within an end of a plug so as to provide resistance against the plug leaving the head. The head preferably has a resilient device, for example a spring loaded ball or, most simply, a resilient wire, for resiliently bearing against the plug. A plug introducer tool preferably has a low-torque handle, that is to say, a handle which provides only a small moment about its axis. Preferably, the handle is of simple bar form, without a cross piece. By this means, it is virtually impossible to force a cross-thread when in the bore of the screw, should the plug be introduced skew.

A plug securement tool has a head adapted to be received within an end of a plug, which head is suitably a close driving fit therein. This head is suitably of plain form, e.g. it does not have a resilient device to aid retention of the plug; this is not required, for the plug is already secure, by virtue of its engagement within the bore of the screw, achieved by use of the plug introducer tool. The plug securement tool preferably has a high-torque handle, for example a handle with a transverse arm, to provide high leverage.

Preferably, the arrangement of the plug and the pad is such that the lower face of the plug may engage the upper face of the pad without contacting means for mechanical engagement of the pad with a pad handling tool. Thus, said means, e.g. the projection or bore, cannot be damaged when the pad is clamped between the plug and the rod, and so, should it be necessary, removal using a pad handling tool can be assured.

The provision of a plug of the type described, and of the associated instrumentation, may be regarded as independent aspects of the present invention.

Suitably, an instrumentation kit for use in relation to a system of the present invention is provided comprising:

a screw insertion tool for engaging the head of the screw to insert the screw into a spinal body;

a plurality of pad handling tools, preferably at least six, whereby a plurality of pads may be located thereon in readiness for an operation;

a plurality of plug introducer tools, preferably at least six, whereby a plurality of plugs may be located thereon in readiness for an operation;

a plug securement tool.

Preferably, the kit further comprises instrumentation to form a hole in a spinal body. Such instrumentation suitably comprises:

a punch to form a depression at a location to be drilled;

a drill bit, having a shoulder corresponding to the maximum depth of the hole required;

a thread-forming tool to form a thread corresponding to that of the screw, in a hole drilled by the drill bit.

Preferably, the kit comprises a probe tool to probe within the hole drilled by the drill bit, for the purpose of testing it. The probe preferably comprises a narrow feeler portion for location within the hole, the end of which is bent transversely to form a feeler head.

Preferably, the kit includes a rod push tool having a head which is curved go as to securely engage, preferably to embrace, a rod. In use, this tool may be engaged with the rod, near to a screw, to hold the rod against the bottom of the passage, whilst the pad and plug are located in the bore of the screw.

Preferably, the kit comprises a rod of a high tensile material acceptable to the human body—for example, stainless steel—and a rod of a more ductile material—for example, aluminiun, which may be used for making a model of the shape of rod required. The kit may further comprise bending equipment for bending a rod to shape.

The screw insertion tool suitably comprises a head to engage, preferably to receive, the head of the screw, the head of the tool having a cross-bar to locate within the slot in driving engagement, the head of the tool having means to provide resistance against the disengagement of the head of the tool from the head of the screw. Such means suitably comprises a resilient device, for example, a resilient wire looped over the cross-bar. The screw insertion tool preferably has a handle with a transverse arm, to provide high leverage. Preferably, the arm is substantially parallel to the cross-bar in the head of the tool, so that the orientation of the arm denotes that of the slot in the head of the screw.

Preferably a tool is provided which may be used for increasing or decreasing the spacing and/or tilt between screws secured in respective spinal bodies, in order to correct tilt, alignment or spacing deformities thereof, the tool comprising a pair of legs, each of which has a distal engagement end adapted to engage a screw, the spacing of the engagement ends being under the control of a control screw.

Suitably, the tool comprises a frame on which each leg is pivotally mounted, and on which the control screw is mounted such that it can turn but not move axially, an internally threaded collar being located on the control screw so as to be moved axially by the turning of the screw, the collar having secured between it and each leg, a respective transverse side arm, each side arm being pivotally mounted to the collar, and pivotally mounted to a leg at a position spaced from the pivot of the leg to the frame. Preferably, the pivot of each leg to the frame is located between the engagement portion, and the pivot of the leg to the side arm; preferably nearer to the pivot of the log to the aide arm. Suitably, one end of each side arm is pivotally mounted to the non-engagement end of the respective log, and the other end of each aide arm is pivotally mounted to the collar.

Preferably, each leg is kinked, towards the other leg, at a position between its pivot to tho frame and its engagement end. Suitably, each leg has an end region incorporating its engagement end, which end region has been bent out of the general plane of the leg, through a small angle.

Preferably, the engagement end of each leg has mounted to it a pin projecting transversely from the leg, the pin being adapted to be securely received in a grooved neck which may be provided at the base of the head of a screw.

Whilst a tool as described above may be used in relation to control the spacing of screws as herein described, it may find uses in other surgical procedures and so may be regarded as an independent aspect of the invention.

Preferably the instrumentation kit incudes at least two x-ray markers for insertion into holes which have been drilled in a spinal body, the markers being used to determine whether the holes are correctly aligned prior to insertion of pedicle screws. The x-ray markers may be of at least two visually distinct types, the first type being for use in holes on the left hand side of a spinal body and the second type being for use on holes on the right hand side of a spinal body.

Preferably the instrumentation kit includes an adjuster tool for fine adjustment of the orientation of the threaded slots of the screws, the adjuster tool having a head in the form of a cross-bar for driving location within the threaded slot and a handle with an arm in a known orientation to the cross-bar in the head of the tool, most conveniently substantially parallel to the cross-bar in the head of the tool, to provide a simple indication and adjustment of the slot orientation.

Suitably, each part of the apparatus described above is of stainless steel. Preferably, each part which is to contact a patient—the screw, pad and plug, and apparatus such as drill bits—is of surgical quality stainless steel, for example conforming to British Standard (BS) 3531/2 1980 COMP B.

The various aspects of the present invention as described above will now be described further, by way of example, with reference to the accompanying drawings, in which.

Figure 1:
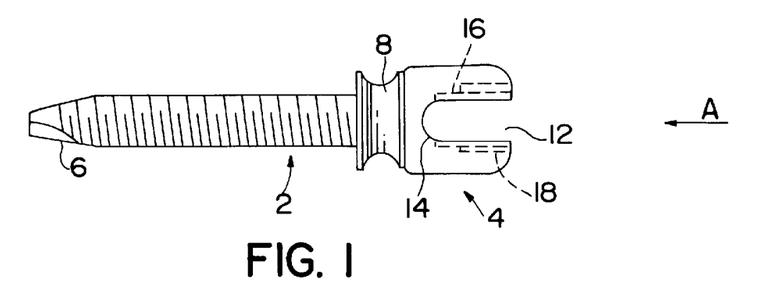
FIG. 1 shows a screw for securement into a vertebra, in side elevation.

The screw shown in FIG. 1 is for location in a pedicle on a vertebra. It has a threaded shank 2 and a head 4. The shank is formed with a tapered cutting nose 6, whereby it may be self-tapping in softer spinal regions, such as the sacrum. Typically, the length of the threaded shank will be 30 mm or 40 mm, and it will be approximately 6 mm in external diameter.

Between the shank 2 and the head 4 is a grooved neck 8.

Figure 2:
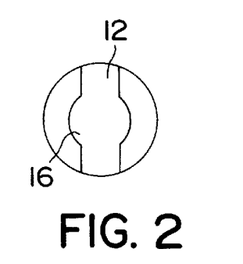
FIG. 2 shows the head of the screw of FIG. 1, looking in the direction of the arrow A.

The head 4 has a slot 12 which is open to the top of the head, and extends across the width of the head, and terminates in a semi-cylindrical bottom wall 14. Within the slot, effectively forming part of the slot, there is a bore 16, which is coaxial with the threaded shank 2. The bore 16 is formed with screw threads denoted by the dotted lines is in FIG. 1, from the top of the bore to a position approximately two thirds of the way down it.

Figure 4:
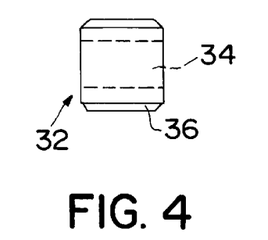
FIG. 4 shows a plug for use with the screw, in side elevation.
Figure 5:
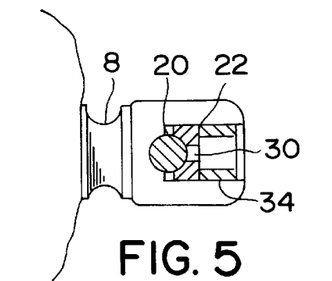
FIG. 5 shows a screw secured to a vertebra with the head projecting.

The slot 12 is of a width to accept passage, just, of a rod 20 (see FIG. 5). The purpose of the screw is to firmly clamp the rod 20 in place, the rod extending perpendicularly of the screw, and extending to one or more other screws, in order to provide spinal support The rod is clamped by means of the pad and plug of FIGS. 3 and 4.

Figure 3:
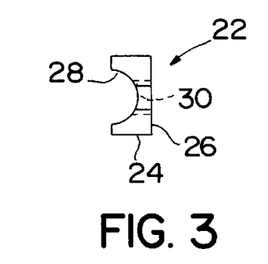
FIG. 3 shows a pad for use with the screw, in side elevation.

The pad 22 has a circularly cylindrical side wall 24, a flat top face 26, and a concave bottom face 28. The curvature of the bottom face 28 matches that of the rod 20. An internally threaded through-bore 30 extends between the faces 26 and 28. The diameter of the pad 22 is such that it can be snugly received within the bore by axial insertion, but such that it cannot then escape sideways, through the side regions of the slot. Removal of the pad thus requires reverse axial movement.

The plug 32 is a grub screw having a through-bore 34 which is hexagonal in cross-section. The external thread 36 of the plug 32 is engageable with the thread 18 formed in the upper region of the bore 16, in the head of the screw.

In the use of the screw, therefore, the threaded shank is engaged within a vertebra, being screwed in until the neck 8 abuts the vertebra. The rod 20 is then located within the slot, the pad is located within the bore, and the plug is screwed into the bore, to press the pad against the rod, until the rod is firmly gripped between the curved bottom wall of the slot and the curved face of the pad.

Figure 11:
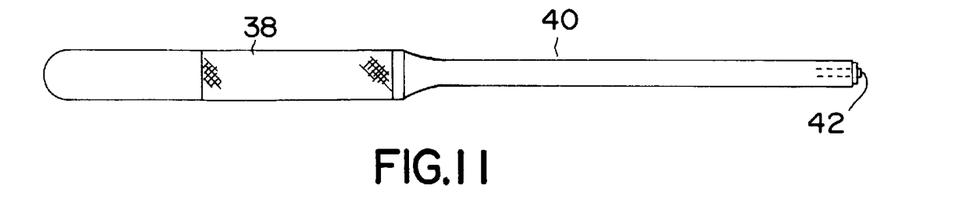
FIG. 11 shows a pad handling tool.
Figure 12:
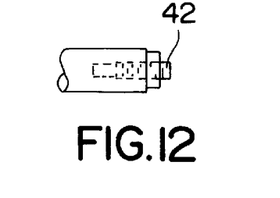
FIG. 12 shows the end of the tool of FIG. 11 in greater detail.

This insertion operation is greatly assisted by means of the threaded through-bore 30 of the pad 22, and of the pad handling tool shown in FIGS. 11 and 12. The pad handling tool has a knurled cylindrical handle region 38 (which does not have any transverse arms or other high-torque means), and a narrower cylindrical nose region 40, to the end of which is secured a threaded projection 42 (see FIG. 12), which can be screwed into the threaded bore 30 of the pad. To insert the pad within the bore, it is engaged on the projection 42 of the pad handling tool and pushed down the bore until its curved face rests on the rod. The pad handling tool is then unscrewed. The pad cannot follow the turning movement of the pad handling tool because of the location of its curved face over the rod. Equally, should it be desired to remove a pad from a bore, the pad handling tool may be used to engage the pad. The externally threaded projection 42 of the pad handling tool is slightly longer than the bore 30 of the pad, so that when insertion is complete, the pad will have been lifted slightly from the rod, though not by so much that it may turn with the turning movement of the pad handling tool.

Figure 13:
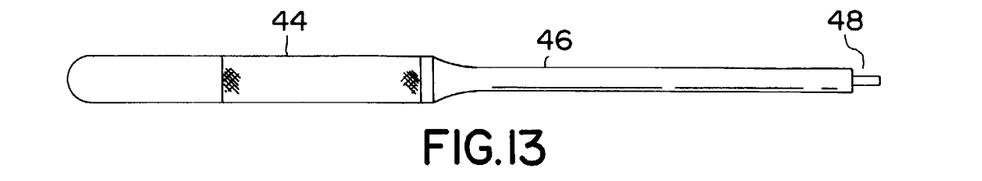
FIG. 13 shows a plug introducer tool.
Figure 14:
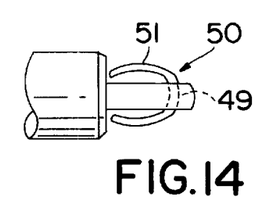
FIG. 14 is an enlarged view of the end of the tool of FIG. 13.
Figure 15:
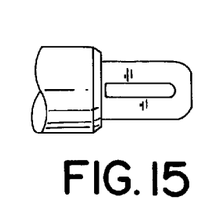
FIG. 15 is a view corresponding to FIG. 14 but in an orthogonal elevation.
Figure 16:
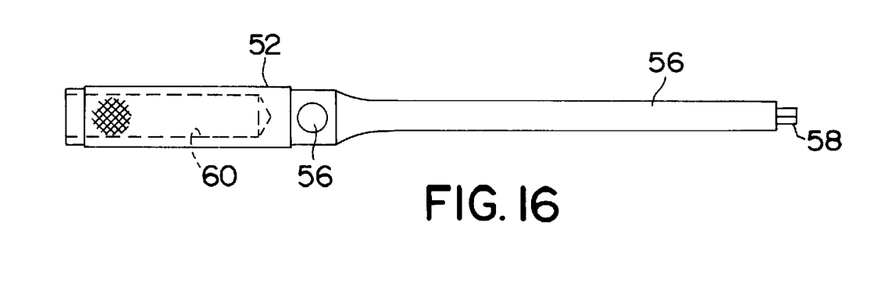
FIG. 16 shows a plug securement tool.

The securement in place of the plug 32 is achieved by use of the plug introducer tool, shown in FIGS. 13 to 15, and the plug securement tool shown in FIG. 16.

The plug introducer tool has a knurled cylindrical handle 44 (which does not have any transverse arms or other high-torque means), and a narrower cylindrical nose region 46. At the end 48 of the nose region 46 there is a rectangular-section projection 48, through the narrower width of which is a bore 49, through which is secured a resilient wire 50. Tho respective ends of the resilient wire 50, which project from the respective sides of the projection 48, at 51, are convexly curved. The arrangement is such that a plug 32 may be engaged on the projection 48, the wider dimension of the projection 48 extending across the bore of the plug between parallel hexagon flats, and each projecting portion 51 of the wire 50 being somewhat compressed, so as to give rise to a resilient force tending to prevent removal of the plug from the projection 48. The introducer tool is used for introducing the plug into the bore 16 of the screw head. Because it has a low-torque handle, it is most unlikely that, should the plug be introduced incorrectly, a cross-thread can be formed.

Once the plug introducer tool has been used to introduce the plug to the bore 16, it is withdrawn, and the plug securement tool of FIG. 16 is engaged with the plug. The plug securement tool has a knurled cylindrical handle 52, which has opposed transverse arms 54 extending to either side of it. A narrower cylindrical nose region 56 leads from the handle, and terminates in a hexagonal-section drive head 58. The drive head 58 having been engaged within the plug, the tool is turned to firmly clamp the rod. By means of the arms 54, a high torque can be generated, so that firm clamping is achieved.

The handle 52 of the plug securement tool has machined in it a bore 60, to reduce weight.

Because the plug 32 is the same at each of its ends, it does not matter which way it is introduced into the bore 16. When it bears against the top face 26 of the pad 22, it does so over an annular area between the pad bore 30 and the circumference of the top face 26. As a result, the thread of the bore, where it terminates at the top face 26, cannot be damaged by the plug 32. Thus, the thread of the bore 30 should always be able to receive the screw-threaded projection 42 of the pad handling tool, should removal be required.

Instrumentation for inserting the screw into a vertebra will now be described with reference to FIGS. 6 to 10.

Figure 6:
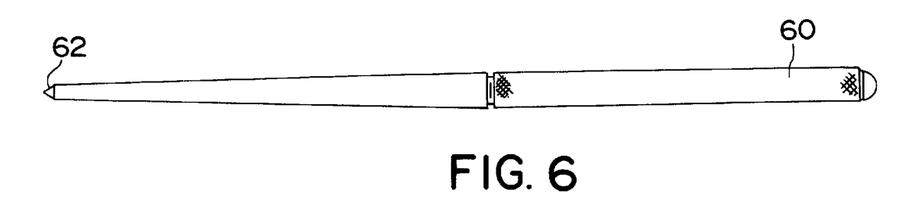
FIG. 6 shows a punch.
Figure 7:
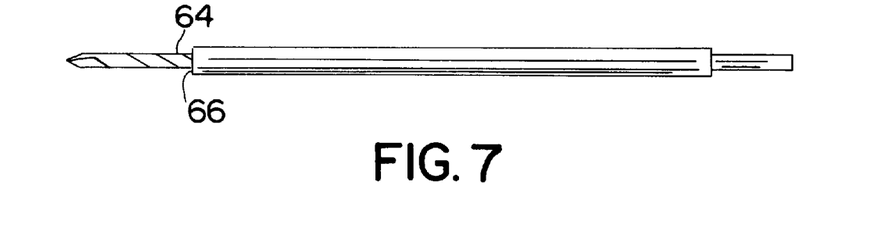
FIG. 7 shows a drill bit.

FIG. 6 shows a punch for forming a depression in a vertebra. The punch has a narrow, cylindrical knurled handle 60 and has a four-facet point 62. Once the depression has been formed by the punch, the drill bit of FIG. 7 can safely be used. The drill bit has a drill head 64, with a diameter slightly less than the internal diameter of the threaded shank 2 of the screw. The drill head 64 is of the length as the shank 2, and terminates at a shoulder 66, which ensures that the correct depth is drilled. In use, the drill bit is generally driven by a hand drill.

Figure 8:
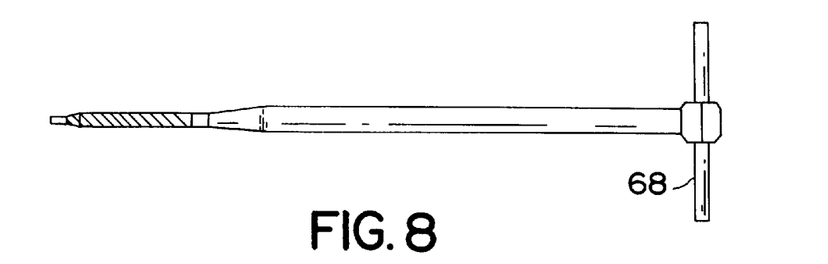
FIG. 8 shows a thread-forming tool.

If drilling has been into the sacrum, the screw can generally now be inserted, and will have a self-tapping action. In other regions of the spine, the thread-forming tool of FIG. 8 is now used, to form a thread corresponding to that of the threaded shank of the screw. To enable the generation of the necessary torque, the thread-forming tool has in its handle region, at the opposite end to the thread-forming part, a cross-bar 68.

Figure 9:
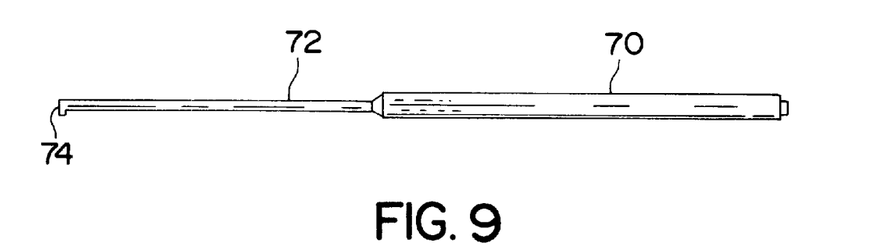
FIG. 9 shows a probe tool.

The probe tool shown in FIG. 9 can be used to assess the drill hole, for example to confirm that it is entirely within bone. The probe tool comprises a handle region 70, secured to a wire feeler region 72, the free end of which has been bent through 90° to form a feeler head 74.

Figure 21:
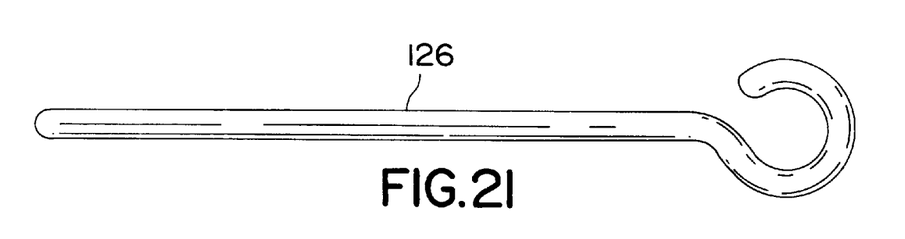
FIG. 21 shows an x-ray marker of a first type.
Figure 22:
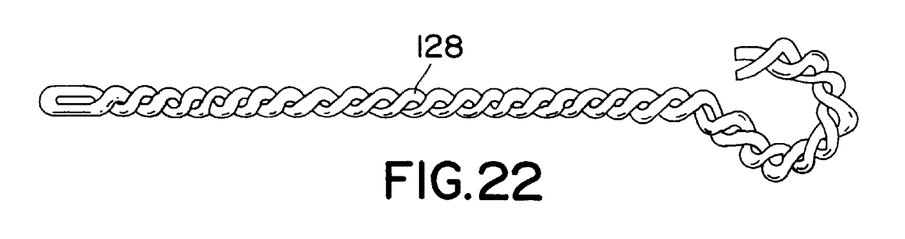
FIG. 22 shows an x-ray marker of a second type.

FIGS. 21 and 22 show markers 126, 128 in the form of steel crooks, about 50 mm long. The markers are used so that, if required, additional confirmation of the alignment of the drilled hole may be obtained by an imaging technique, for example x-ray, the markers showing up on the image. Markers 126 for holes on the left hand side of the spine are plain, FIG. 21, and the markers 128 for holes on the right hand side are fluted, FIG. 22, having been formed by a twisting operation. In use the markers are inserted into the drilled holes and an image is taken. The alignment of the holes can then be confirmed with the plain/fluted markers for left/right aiding interpretation of the image.

Figure 10:
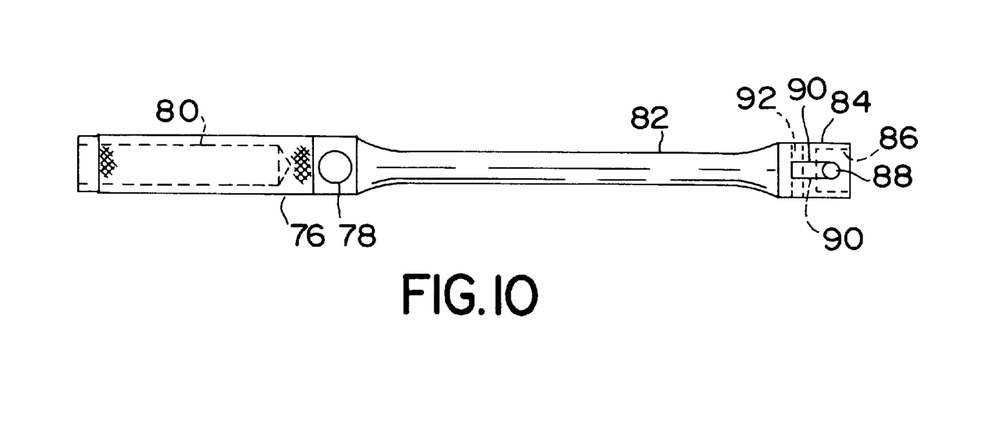
FIG. 10 shows a screw insertion tool.

After these operations, a screw can be inserted into the hole, using the screw insertion tool shown in FIG. 10. The screw insertion tool has a knurled cylindrical handle region 76, with opposed transverse arms 78, to enable the generation of high torque. For reasons of lightness, the handle region 76 has been machined to form a bore 80. The handle region 76 leads to a narrower cylindrical nose region 82, which broadens, to terminate in a head 84, to receive the head of the screw. The head 84 has a cylindrical socket 86 across which a cross-bar 88 is diametrically mounted. The base of the socket is formed With two narrow, longitudinal passages 90, which lead to a narrow cross-bore 92. A resilient wire extends from the cross-bore 92, through one passage 90, over the cross-bar 88, through the other hole 90, and back to the bore 92. By means of this resilient wire, the screw insertion tool securely retains the head of the screw, with the slot of the screw being located over the cross-bar 88, and resiliently displacing the wire.

Figures 23, 24:
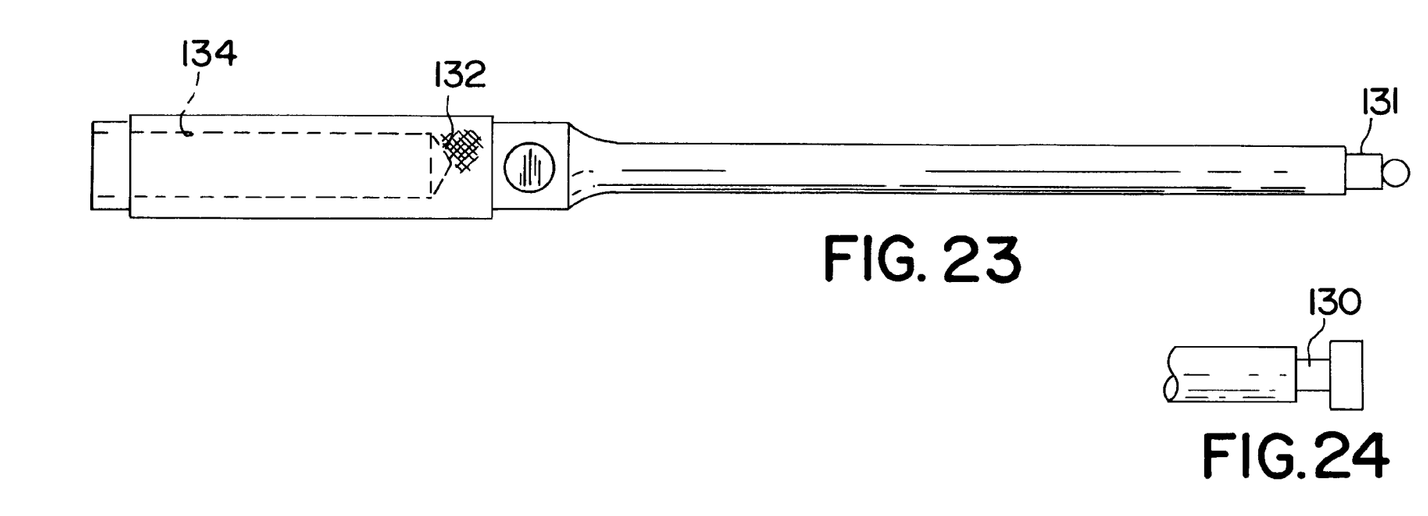
FIG. 23 shows a side view of an adjuster tool.
FIG. 24 shows a plan view of the end portion of the adjuster tool of FIG. 23.

Once the screw has been inserted fine adjustment of the alignment of the slot 12 for receiving the rod 20 can be achieved by use of the adjuster tool of FIGS. 23 and 24. The adjuster tool has a T-shaped head 130 which fits into the slot of the screw and, by means of the knurled handle region 132 and its opposed transverse arms 134 extending to either side of it, parallel to the slot. The alignment of the slot may be adjusted so as to align as closely as possible with the slots of its neighbouring screws and thereby facilitate insertion of the rod 20.

The handle 132 of the adjuster tool has machined in it a bore 134 to reduce weight.

Figure 17:
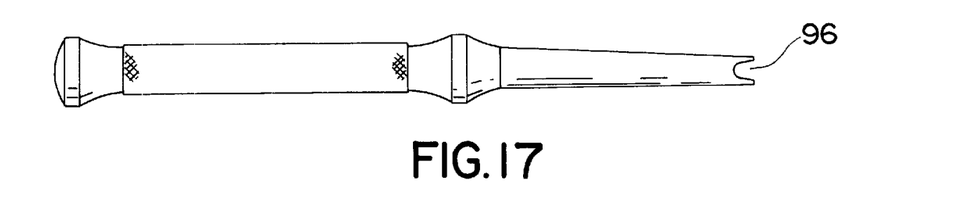
FIG. 17 shows a rod push tool.

Whilst the pad and plug are being inserted, it may be necessary to push the rod 20 into position at the base of the slot 12. The rod push tool shown in FIG. 17 enables this to be easily achieved. The rod push tool has a concave nose region 96, within which the rod can be securely received, with the rod push tool being engaged with the rod slightly to one side of the screw.

Figure 18:
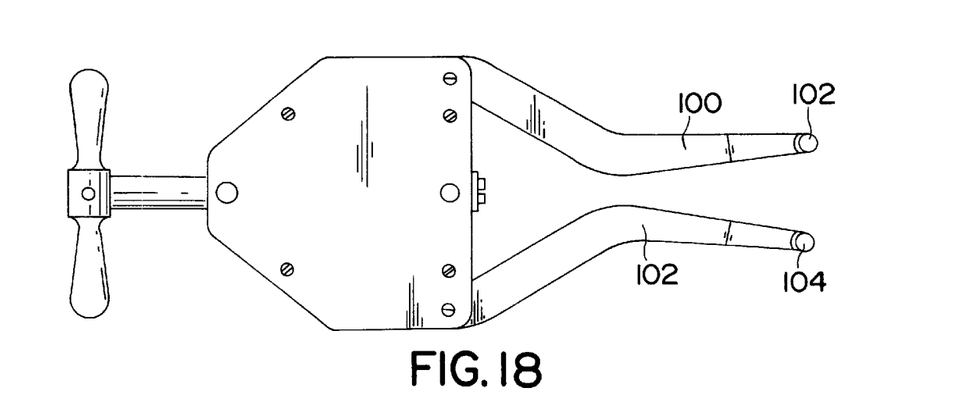
FIG. 18 shows a distracter/compressor tool for altering the spacing between screws, in plan view.

During a surgical procedure, it will typically be necessary to secure several screws in place, to adjoining vertebrae and/or the sacrum, and it may be desirable to use the screws, once located, to alter the tilt, alignment or spacing of the bodies to which they are attached. This may be aided by use of the distracter/compressor tool shown in FIGS. 18, 19 and 20. Essentially, this comprises a pair of legs 100, 102 the free end of each of which terminates in a spool-shaped pin 102, 104. Each pin is engageable within the grooved neck 8 of a screw. The pins 102, 104 may be located outside screws, and be moved towards each other to push the screws towards each other, in which position the rod may be fixed. Alternatively, they may be located between two screws, and moved apart, to move the screws apart, in which position the rod may be fixed.

Figure 19:
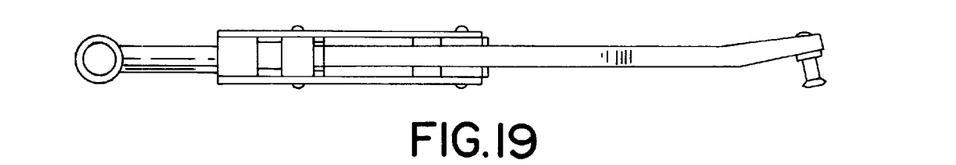
FIG. 19 is a side elevation of the tool of FIG. 18.
Figure 20:
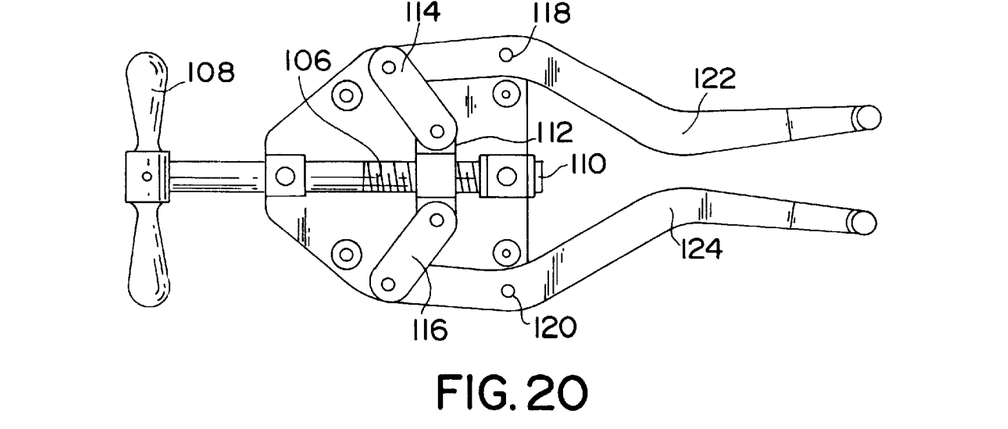
FIG. 20 is a plan view corresponding to that of FIG. 18, with a cover plate removed.

The mechanism, shown in FIG. 20, comprises a threaded control screw 106, which is rotatable by means of handle 108, but restrained by an axial pivot screw arrangement 110 against axial movement. Engaged with the control screw 106 is an internally threaded collar 112, which is free to move axially. It will be appreciated that turning the control screw 106 causes movement of the collar 112 along the control screw. To each side of the collar is pivoted the inner end of a respective side arm 114, 116. The other end of each side arm is pivoted to the non-engagement end of a respective leg. Each leg is pivoted to a frame about a respective pivot 118, 120, located closer to the non-engagement end than to the engagement end of the respective leg. Between respective pivot 118, 120 and the engagement end of the respective leg, the leg is kinked at 122, 124, towards the other leg. As shown in FIG. 19, the engagement end region of each leg is bent upwardly through a small angle, relative to the general plane of the leg, in order to achieve the optimal angle for use.

The apparatus required to be available for any given surgical procedure may include the following:
 the required number of screws, pads and plugs;
 a punch, a drill bit and a thread-forming tool;
 a probe tool;
 plain and fluted x-ray markers as required;
 pad handling tools corresponding in number to the number of pads required, with each pad being pre-engaged on a pad handling tool;
 plug introducer tools corresponding in number to the number of plugs required, with each plug being pre-engaged on a plug introducer tool;
 a plug securement tool;
 a screw insertion tool;
 an adjuster tool;
 a rod push tool;
 a distracter/compressor tool;
 stainless steel rod.

Additionally, there may be a tool for bending the stainless steel rod to the required shape, and there may be a rod of a ductile material, for example aluminium, to form a model of the rod shape required.

The reader's attention is directed to all papers and documents which are filed concurrently with or previous to this specification and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

I claim:

1. A spinal fixation system comprising:
 (A) a plurality of screws adapted to engage spinal bodies and a common elongate member adapted for attachment to the screws, each screw having a threaded shank for anchoring the screw to the respective spinal body and a head for attachment to the elongate member, the head having a top, having a width, and having an internally threaded passage which is open to the top of the head and extends across the width of the head so as to accept the elongate member;

(B) a plurality of pads to provide a pad for each screw, the pads being adapted for location within the respective passages of each screw and each pad having a bottom surface adapted to engage the elongate member;

(C) a plurality of externally threaded plugs to provide an externally threaded plug for each screw, the plugs being adapted to be screwed into the respective passages of the screws to engage the upper surface of the pads and secure the pads and the elongate member in position;

(D) and each pad being adapted for attachment, release, and re-attachment to a pad handling tool;

whereby each pad can be located within the passages and removed therefrom by attachment, release, and re-attachment to the pad handling tool.

2. A spinal fixation system according to claim 1 wherein each pad has an internally threaded bore adapted for attachment to a complimentary externally threaded projection of the pad handling tool.

3. A spinal fixation system according to claim 1 wherein the elongate member has a surface contour and the bottom surface of each of the pads is contoured to substantially match the surface contour of the elongate member.

4. A spinal fixation system according to claim 1 wherein each plug has two ends of identical form, both being adapted to receive within them an engagement portion of a plug insertion tool.

5. A spinal fixation system according to claim 4 wherein both ends of each plug provide a hexagonal socket.

6. A spinal fixation system according to claim 4 wherein each plug has a through bore.

7. A spinal fixation system according to claim 4 wherein the engagement portion has retaining means for positively retaining each respective plug on the engagement portion of the plug insertion tool.

8. A spinal fixation system according to claim 7 wherein the retaining means comprises a resilient wire carried by the engagement portion of the plug insertion tool.

9. An instrumentation kit for a spinal fixation system comprising:

(A) a spinal fixation system having:
a plurality of screws adapted to engage spinal bodies and a common elongate member adapted for attachment to the screws, each screw having a threaded shank for anchoring the screw to the respective spinal body and a head for attachment to the elongate member, the head having a top, having a width, and having an internally threaded passage which is open to the top of the head and extends across the width of the head so as to accept the elongate member,
a plurality of pads to provide a pad for each screw, the pads being adapted for location within the respective passages of each screw and each pad having a bottom surface adapted to engage the elongate member,
a plurality of externally threaded plugs to provide a plug for each screw, the plugs being adapted to be screwed into the respective passages of the screws to engage the upper surface of the pads and secure the pads and the elongate member in position,
and each pad being adapted for attachment, release and re-attachment to a pad handling tool, whereby each pad can be located within the passages and removed therefrom by attachment, release, and re-attachment to the pad handling tool;

(B) a screw insertion tool for engaging the head of each screw to insert the screw in the respective spinal body;

(C) a plurality of pad handling tools for prior location thereon of the plurality of pads in readiness for an operation;

(D) a plurality of plug introducer tools for prior location thereon of the plurality of plugs in readiness for introduction of the plugs into the respective passages of the plurality of screws; and (E) a plug securement tool for tightening the plurality of plugs within the respective passages of the plurality of screws.

10. An instrumentation according to claim 9 further comprising at least two markers for insertion into holes which have been drilled in a spinal body, the markers being used to determine, from an image produced by an imaging system, whether the holes are correctly aligned prior to insertion of screws.

11. An instrumentation kit according to claim 10 wherein at least two visually distinct types of markers are provided, the first type being for use in holes on the left hand side of a spinal body and the second type being for use in holes on the right-hand side of a spinal body.

12. An instrumentation kit according to claim 9 further including instrumentation to form a hole in each respective spinal body, such further instrumentation comprising:

a punch to form a depression in the respective spinal body at a location to be drilled to form the hole;

a drill bit, having a shoulder corresponding to the maximum depth of the hole required; and a thread forming tool for the formation of a thread, corresponding to that of each screw, in the hole to be drilled by the drill bit.

13. An instrumentation kit according to claim 12 further including an adjuster tool for fine adjustment of orientation of the thread formed by the thread forming tool, the adjuster tool having a head in the form of a cross-bar for driving location within the thread and a handle with a transverse arm substantially parallel to the cross-bar in the head of the tool.

14. An instrumentation kit according to claim 12 further including a probe tool to probe within the hole to be drilled by the drill bit to confirm that the hole is entirely within bone, at both bottom and sides.

15. An instrumentation kit according to claim 14 wherein the probe includes an end having a feeler portion for location within the hole, the end of the probe being bent transversely to form a feeler head on the feeler portion.

16. An instrumentation kit according to claim 9 further including a rod push tool having a head for engagement with the elongate member, the rod push tool being used to urge the elongate member into the passage of each screw.

17. An instrumentation kit according to claim 16 wherein the head of the rod push tool is curved to embrace the elongate member and hold the elongate member at the bottom of the passage of each screw, whilst each pad and plug are located in the passage of each screw.

18. An instrumentation kit according to claim 9 wherein the elongate member comprises a rod of a high tensile material acceptable to the human body.

19. An instrumentation kit according to claim 18 wherein the high tensile material is stainless steel.

20. An instrumentation kit according to claim 9 further including a length of ductile material which is used for making a model of the shape of the elongate member required.

21. An instrumentation kit according to claim 20 wherein the ductile material is aluminium.

22. An instrumentation kit according to claim 9 wherein the screw insertion tool has a head to engage the head of each screw, the head of the screw insertion tool having a cross-bar to locate within the head of each screw in driving engagement and means to provide resistance against the disengagement of the head of the screw insertion tool from the head of each screw.

23. An instrumentation kit according to claim 22 wherein the means to provide resistance against the disengagement of the head comprises a resilient wire looped over the cross-bar.

24. An instrumentation kit according to claim 22 wherein the screw insertion tool has a handle with a transverse arm substantially parallel to the cross-bar in the head of the tool.

25. An instrumentation kit according to claim 9 further comprising a distractor/compressor tool for increasing and decreasing spacing and tilt between respective screws secured in respective spinal bodies.

26. An instrumentation kit according to claim 25 wherein the distractor/compressor tool includes a pair of legs, each of which has a distal engagement end adapted to engage a screw, spacing between the engagement ends being under the control of the screw.

27. An instrumentation kit for a spinal fixation system comprising:

(A) a spinal fixation system having:
a plurality of screws adapted to engage spinal bodies and a common elongate member adapted for attachment to the screws, each screw having a threaded shank for anchoring the screw to the respective spinal body and a head for attachment to the elongate member, the head having a top, having a width, and having an internally threaded passage which is open to the top of the head and extends across the width of the head so as to accept the elongate member,
a plurality of pads to provide a pad for each screw, the pads being adapted for location within the respective passages of each screw and each pad having a bottom surface adapted to engage the elongate member,
a plurality of externally threaded plugs to provide a plug for each screw, the plugs adapted to be screwed into the respective passages of the screws to engage the upper surface of the pads and secure the pads and the elongate member in position,
and each pad being adapted for attachment, release, and re-attachment to a pad handling tool.
whereby each pad can be located within the passages and removed therefrom by attachment, release, and re-attachment to the pad handling tool;

(B) a screw insertion tool for engaging the head of each screw to insert the screw in the respective spinal body;

(C) a plurality of pad handling tools for prior location thereon of the plurality of pads in readiness for an operation;

(D) a plurality of plug introducer tools for prior location thereon of the plurality of plugs in readiness for introduction of the plugs into the respective passages of the plurality of screws;

(E) a plug securement tool for tightening the plurality of plugs within the respective passages of the plurality of screws; and (F) a distractor/compressor tool for increasing and decreasing spacing and tilt between respective screws secured in respective spinal bodies; wherein the distractor/compressor tool includes a pair of legs, each of which has a distal engagement end adapted to engage a screw, spacing between the engagement ends being under the control of the screw, and the distractor/compressor tool includes a frame on which each leg is pivotally mounted, and on which the screw is mounted such that it can turn but not move axially, and the screw having an internally threaded collar located on the screw so as to be moved axially by the turning of the screw, the collar having secured between it and each leg, a respective transverse side arm, each side arm being pivotally mounted to the collar, and pivotally mounted to the leg at a position spaced from the pivot of the leg to the frame.

28. An instrumentation kit according to claim 27 wherein pivoting of each leg to the frame of the distractor/compressor tool is located between the engagement portion and the side arm.

29. An instrumentation kit according to claim 27 wherein the side arm has two ends and one end of each side arm is pivotally mounted to the non-engagement end of the respective leg, and the other end of each side arm is pivotally mounted to the collar.

30. An instrumentation kit according to claim 27 wherein each leg is kinked towards the other leg at a position between its pivot to the frame and its engagement end.

31. An instrumentation kit according to claim 27 wherein each leg has an end region incorporating its engagement end, which end region is bent out of the general plane of the leg, through a small angle.

32. An instrumentation kit according to claim 27 wherein the engagement end of each leg has mounted to it a pin projecting transversely from the leg, the pin being adapted to be securely received in a grooved neck which is provided at the base of the head of screw.

\* \* \* \* \*